United States Patent [19]

Law et al.

[11] 4,306,864
[45] Dec. 22, 1981

[54] COMBINATION AMALGAM DISPENSER AND PLUGGER

[75] Inventors: Franklin E. Law, Adelphi, Md.; Hazel Harper, 2139 Georgia Ave., NW., Washington, D.C. 20001

[73] Assignee: Hazel J. Harper, a part interest

[21] Appl. No.: 201,629

[22] Filed: Oct. 28, 1980

[51] Int. Cl.³ ............................................. A61C 3/08
[52] U.S. Cl. ....................................... 433/83; 433/164
[58] Field of Search ...................... 433/90, 164, 83, 89

[56] References Cited
U.S. PATENT DOCUMENTS 2,476,793  7/1949  Arena ...................................... 433/90

Primary Examiner—H. McBride
Attorney, Agent, or Firm—Lane, Aitken, Kice & Kananen

[57] ABSTRACT

A dental implement for dispensing amalgam includes a handle on which are mounted at least one amalgam dispenser and a plugger corresponding to each amalgam dispenser for condensing the amalgam dispensed by the dispenser.

6 Claims, 5 Drawing Figures

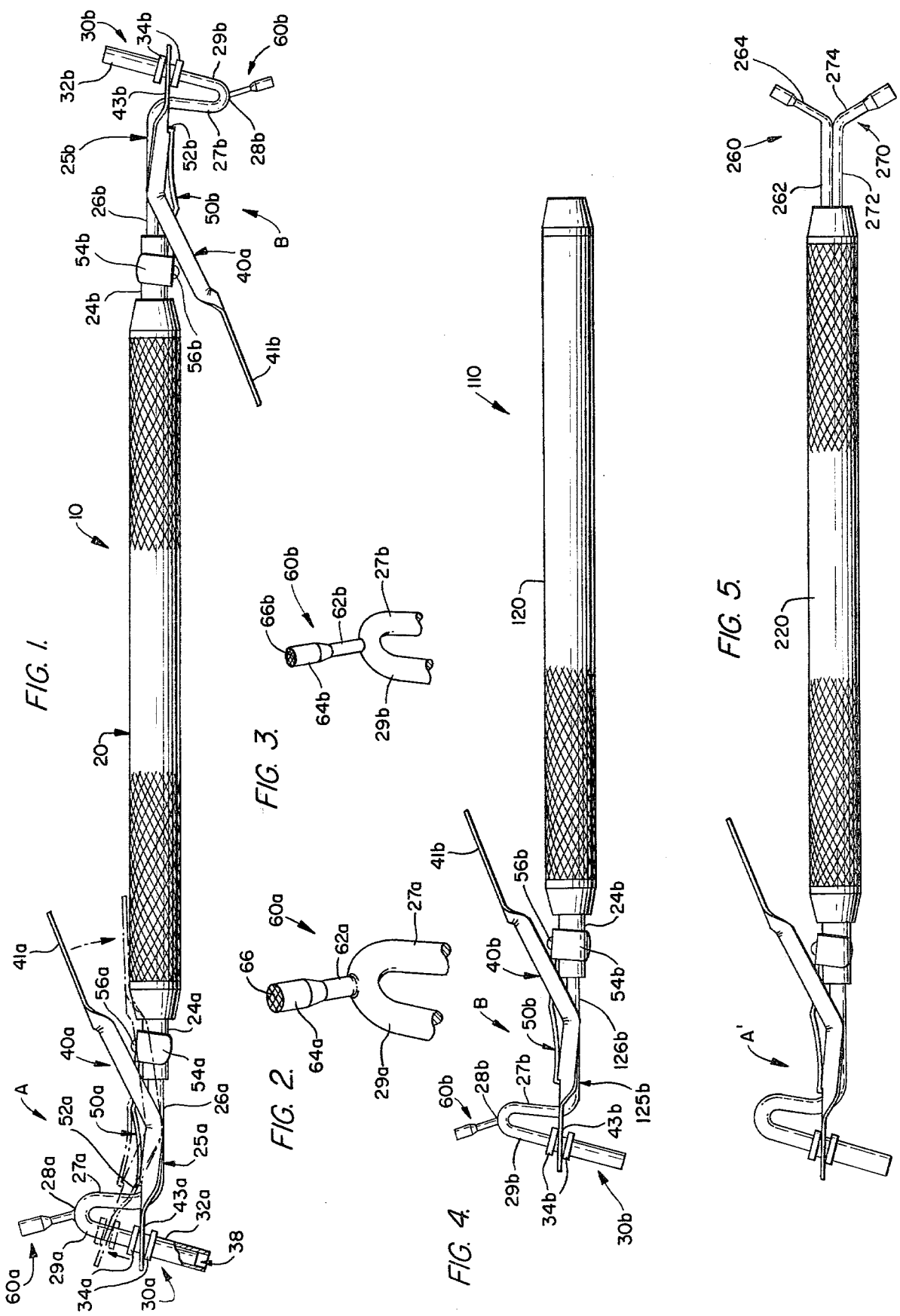

COMBINATION AMALGAM DISPENSER AND PLUGGER

BACKGROUND OF THE INVENTION

This invention is directed to a dental implement for dispensing and condensing amalgam into a tooth cavity. In particular, it is directed to an amalgam dispenser having a plugger extending from the dental implement for condensing the amalgam into the dental cavity.

An amalgam dispenser that has been commercially accepted is described in U.S. Pat. No. 1,797,866, issued to C. S. Ivory on Mar. 24, 1931. It has been common practice when using a lever-operated dispenser of this type to use another implement to condense the amalgam. Although the Ivory patent suggests at page 2, lines 47–65, using the dispenser to pack the amalgam by holding the lever against the handle, it is apparent that this method is operationally and functionally self-limiting. To overcome the disadvantages attendant with the Ivory suggestion, our copending application, Ser. No. 201,620, filed Oct. 28, 1980, discloses an amalgam dispensing component with corresponding condensing element utilizing a common handle.

While it may be desirable for a number of dental practitioners to use a lever-operated dental implement as described in our copending application, a need has existed for providing a lever-operated dispenser with a plugger as a separate element of the dental implement.

Accordingly, it is one objective of the present invention to improve the compacting procedure by providing an amalgam dispenser having a plugger extending from the dispensing rod for condensing the amalgam into the tooth cavity.

It is another objective of the present invention to improve the compacting procedure by orienting the plugger with respect to the amalgam dispenser such that the dental practitioner may conveniently change from dispensing the amalgam to condensing the amalgam in the tooth cavity, by rotating the instrument from one working position to the other.

SUMMARY OF THE INVENTION

Directed toward achieving these and other objectives, one embodiment of the dental implement of the present invention includes a handle having amalgam dispensing rods extending from each end of the handle. Each dispensing rod is a part of an amalgam dispensing and condensing assembly, the dispensing rod being secured to the handle and having a plugger extending therefrom. Mounted on each dispensing rod is a tubular amalgam carrier engaged by a spring-biased finger-operated lever.

In practice, a suitable amount of amalgam is placed in one amalgam carrier. With the implement held in position adjacent the tooth cavity, the lever is depressed, raising the carrier on the amalgam dispensing rod and thereby releasing the amalgam. The implement may then be used to condense the amalgam by rotating the handle 180° so that the plugger is adjacent the tooth cavity in position for condensing the amalgam.

In another embodiment, the dental implement includes a single amalgam dispensing and condensing assembly supported at one end of the handle.

A third embodiment includes an amalgam dispensing assembly on one end of the handle and a pair of individual pluggers extending from the opposite end of the handle.

BRIEF DESCRIPTION OF THE DRAWINGS

In the drawings:

FIG. 1 is a side elevational view of the combination amalgam dispenser and plugger according to the present invention;

FIG. 2 is an enlarged perspective view of the large plugger of FIG. 1;

FIG. 3 is an enlarged perspective view of the small plugger of FIG. 1;

FIG. 4 is a side elevational view of the combination amalgam dispenser and plugger according to another embodiment of the present invention; and FIG. 5 is a side elevational view of the combination amalgam dispenser and plugger according to still another embodiment of the present invention.

DETAILED DESCRIPTION OF THE PREFERRED EMBODIMENTS

As illustrated in FIGS. 1–3, reference character 10 refers, in general, to the dental implement in accordance with the preferred embodiment of the present invention. The dental implement 10 includes a handle 20 which tapers at both ends to rounded front portions 24a and 24b, each of which has a central bore for receiving a reduced diameter amalgam dispensing rod designated in general by the reference characters 25a and 25b, respectively. The dispensing rods 26a and 26b have shank portions 26a and 26b extending outwardly from front portions 24a and 24b, respectively, along the longitudinal axis of the handle 20. The description which follows pertains to the dispensing rod 25a although it will be understood that the description applies likewise to the dispensing rod 25b, provided allowance is made for the fact that a portion of the dispensing rod 25b is inverted with respect to the dispensing rod 25a.

The forward end of the dispensing rod 26a includes an upwardly curving transverse portion 27a, a curved portion 28a defining an arc, and an oblique portion 29a extending downwardly to a point where the end of the dispensing rod 25a, illustrated in broken perspective in FIG. 1, lies below the longitudinal axis of the handle 20. The oblique portion 29a of the dispensing rod 25a forms an acute angle with respect to the longitudinal axis of the handle 20. The angular orientation of the oblique portion 29a enables the dental implement 10 to dispense the amalgam more effectively in the difficult to reach dental recesses.

Amalgam dispensing and condensing assemblies A and B are inverted with respect to one another as shown in FIG. 1 and are located on opposite ends of the dental implement 10. Assembly A provides a larger amalgam carrying capacity than assembly B, although the operation and elements of each are identical.

The following description applies to assembly A with the understanding that the description applies likewise to assembly B. The amalgam dispensing and condensing assembly A includes an amalgam carrier 30a, a lever member 40a, a spring 50a, and a larger plugger 60a.

The amalgam carrier 30a comprises a tubular member 32a provided with upper and lower flanges 34a that are spaced apart from one another. When the lever member 40a is in its normally raised position, the amalgam carrier 30a is in its normally lowered position. The space 38 between the end of the dispensing rod 25a and the end of the tubular member 32a forms a chamber for receiving a suitable amount of amalgam for subsequent dispensing into the dental cavity.

The lever member 40a includes a rear finger piece 41a which is cut out to clear the rear portion of the spring 50a. The front end of the lever 40a defines a flat portion 43a which includes a slot. The slot has a rear wall, a central enlarged opening, and reduced end openings for receiving the amalgam carrier 30a. The upper and lower flanges 34a of the amalgam carrier 30a are of such a diameter that they pass through the central enlarged opening but not through the reduced end openings of the slot. In this manner, the front end of the flat portion 43a engages the amalgam carrier 30a between the upper and lower flanges 34a. When the finger piece 41a of the lever 40a is lowered from the normally raised position to the lowered position adjacent the handle 20, as shown in broken line perspective in FIG. 1, the flat portion 43a exerts an upward force on the upper flange. Consequently, the amalgam carrier 30a is raised and a segment of the oblique portion 29a of the dispensing rod 25a extends beyond the end of the amalgam carrier 30a. If amalgam were in the chamber between the end of the dispensing rod 25a and the end of the amalgam carrier 30a, lowering of the lever 40a to a position adjacent the handle would release the amalgam from the carrier 30a.

The flat spring 50a has a downwardly-depending lip 52a at its forward end and a rear clip portion 54a that is attached by a screw 56a or by conventional fastening techniques to the rounded front portion 24a of the handle 20. The lip 52a bears upon and overlaps the rear wall of the slot in the lever 40a. This spring action urges the front portion of the lever in a downward direction thus maintaining the amalgam carrier 30a in its lowered position.

The large plugger 60a extends upwardly at an angle from the dispensing rod 25a. As illustrated in FIG. 2, the plugger 60a comprises a cylindrical extension member 62a which flares to a compaction portion 64a. The compaction portion 64a has a generally cylindrical shape which has at one end a compacting tip 66a which is typically serrated to provide a gripping surface more suitable for condensing the amalgam. The plugger 60a may be formed as an integral extension of the arc defined by the curved portion of dispensing rod 26a. As illustrated in FIG. 1, the plugger 60a extends outwardly at 28a, forming an acute angle with the vertical axis drawn through the apex of the curved portion 28a of the dispensing rod 25a and lies in the same plane as the dispensing rod 25a. Further, the plugger 60a forms an obtuse angle with respect to the oblique portion 29a of the dispensing rod 25a. This particular orientation allows the operator to control the condensing operation without interference from the amalgam carrier 30a.

In operation, after the amalgam has been dispensed into the tooth cavity by depressing the finger piece 41a of the lever 40a, the dental implement 10 is inverted and the compacting tip 66a of the plugger 60a is used to condense the amalgam to the proper degree of firmness. If a smaller compacting surface is required, the smaller plugger 60b, as shown in FIG. 3, may be used.

FIG. 4 illustrates a second embodiment of the present invention in which a single amalgam dispensing and condensing assembly, the smaller assembly B, cooperates with a dispensing rod 126b which extends from the handle 120. The other end of the handle 120 does not support a dispensing and condensing assembly. The reference characters from the assembly B of FIG. 1 refer to corresponding identical parts of the amalgam dispensing and condensing assembly B in FIG. 4. It will be apparent that the larger amalgam dispensing and condensing assembly A may be substituted for the smaller assembly B without departing from the spirit of this embodiment. Further, the dispensing and condensing operations of the dental implement 110 as shown in FIG. 4 are identical to that of the dental implement 10 described above.

A third embodiment is illustrated in FIG. 5 and includes a dental implement having a dispensing assembly A' operative at one end of the handle 220. Extending from the opposite end of the handle 220 are two pluggers 260 and 270, respectively, the former having a smaller cross-sectional diameter than the plugger 270.

The smaller plugger 260 and the larger plugger 270 extend outwardly along the longitudinal axis of the handle 220 as indicated at 262 and 272, respectively, and then diverge with the smaller plugger 260 pointing upwardly at 264 and the larger plugger 270 extending in a downward direction at 274. Both pluggers 260 and 270 lie approximately in the same vertical plane and form correspondingly different angles with respect to a horizontal axis along the handle 220.

The amalgam dispensing assembly A' corresponds to the larger assembly A as depicted in FIG. 1 with the exception that the assembly A' does not include the plugger 60a shown extended from the dispensing rod 26a.

In operation, after the amalgam has been dispensed, the end of the dental implement having the pluggers 260 and 270 is inserted into the patient's mouth in order to condense the amalgam. Depending on the size of the tooth cavity, the appropriate plugger, either the smaller plugger 260 or the larger plugger 270, is selected and used to condense the amalgam into the tooth cavity.

The embodiments described are intended to be illustrative, rather than restrictive, the scope of the invention being defined by the appended claims which are intended to embrace all other equivalents, variations, and modifications thereto to which the claims apply.

What is claimed is:

1. In a dental implement for dispensing amalgam, said implement having a handle, a lever mounted on said implement, an amalgam carrier engaging the lever, a dispensing rod extending from one end of the handle, a portion of the dispensing rod cooperating with the amalgam carrier to dispense the amalgam, a spring having a rear end secured to the handle and a front end engaging the lever to maintain the carrier in a normally lowered position so that by operating the lever the amalgam carrier is raised and the dispensing rod extends beyond the amalgam carrier, thereby acting to discharge the amalgam, the improvement comprising:
   means extending from said dispensing rod for condensing the amalgam into the tooth cavity.

2. The dental implement of claim 1 wherein said condensing means comprises a plugger having a longitudinal dimension greater than its cross-sectional thickness, said plugger extending from said dispensing rod.

3. The dental implement of claim 2 wherein said plugger lies in the same plane as said dispensing rod so that said plugger forms an obtuse angle with said portion of said dispensing rod, said plugger including:
   a compacting tip having an exposed surface for condensing the amalgam into the dental cavity.

4. The dental implement of claim 1 wherein said means for condensing the amalgam comprises a pair of pluggers extending outwardly along the longitudinal axis of said handle opposite said end of the handle having said dispensing rod, one of said pluggers having a cross-sectional diameter greater than the other of said pluggers.

5. The dental implement of claim 4 wherein each of said pluggers further comprises a compacting tip extending away from said longitudinal axis of said handle so that the dental implement may be revolved about said longitudinal axis of said handle to bring one of said pluggers into operative condensing position adjacent the tooth cavity.

6. A dental implement for dispensing amalgam comprising in combination:
 a handle;
 a lever mounted on the dental implement;
 an amalgam carrier engaging said lever;
 a dispensing rod extending from one end of said handle, said dispensing rod having:
  a shank portion extending outwardly along the longitudinal axis of said one end of said handle, a transverse portion extending away from said longitudinal axis of said handle,
  an oblique portion oriented at an acute angle to said longitudinal axis of said handle, and
  a curved portion forming an arc connecting said transverse portion and said oblique portion;
 a spring having a rear end secured to said handle and a front end engaging said lever to maintain said amalgam carrier in a normally lowered position so that by operating said lever said amalgam carrier is raised and a segment of said oblique portion of said dispensing rod extends beyond said amalgam carrier, thereby acting to discharge the amalgam; and
 a plugger extending outwardly from said curved portion of said dispensing rod and forming an obtuse angle with said oblique portion so that after the amalgam is dispensed, the dental implement may be inverted to position said plugger in proximity to the tooth cavity for condensing the amalgam.

* * * * *